United States Patent [19]
Akers et al.

[11] Patent Number: 6,115,632
[45] Date of Patent: *Sep. 5, 2000

[54] DUAL CHAMBER PULSE GENERATOR WITH PERIODIC PMT CONTROL

[75] Inventors: Brian P. Akers, Milwaukee, Wis.; John M. Adams, Issaquah, Wash.

[73] Assignee: Cardiac Pacemakers, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/099,045

[22] Filed: Jun. 17, 1998

[51] Int. Cl.$^7$ ............................................. A61N 1/365
[52] U.S. Cl. ........................................ 607/9; 607/17
[58] Field of Search ................... 607/9, 14, 17, 607/18, 25

[56] References Cited

U.S. PATENT DOCUMENTS

| | | | |
|---|---|---|---|
| 5,103,820 | 4/1992 | Markowitz | 607/9 |
| 5,282,465 | 2/1994 | Van Der Veen et al. | 607/17 |
| 5,312,445 | 5/1994 | Nappholz et al. | 607/9 |
| 5,312,450 | 5/1994 | Markowitz . | |
| 5,395,396 | 3/1995 | Lindgren et al. | 607/9 |
| 5,476,485 | 12/1995 | Weinberg et al. . | |
| 5,507,783 | 4/1996 | Buchanan . | |
| 5,658,320 | 8/1997 | Betzold et al. . | |
| 5,725,562 | 3/1998 | Sheldon | 607/19 |
| 5,814,083 | 9/1998 | Hess et al. | 607/14 |
| 5,861,007 | 1/1999 | Hess et al. . | |

OTHER PUBLICATIONS

Calfee, Richard V. (1988). Pacemaker–mediated tachycardia: Engineering solutions. *PACE*, 11, pp. 1917–1928.

Duncan, J. L., and Clark, M. F. (1988). Prevention and Termination of Pacemaker–Mediated Tachycardia in a New DDD Pacing System (Siemens–Pacesetter Model 2010T). *PACE*, 11, pp. 1679–1683.

Fontaine, J. M., Maloney, J.D., Castle, L. W., and Morant, V. A., (1986). Noninvasive assessment of ventriculo–atrial conduction and early experience with the tachycardia termination algorithm in pacemaker–mediated tachycardia. *PACE*, 9, pp. 212–212.

Lamaison, D., Girodo, S., and Limousin, M. (1988). A new algorithm for a high level of protection against pacemaker–mediated tachycardia. *PACE*, 11, pp. 1715–1721.

Marks, M.S. (1997). InControl; Freedom to operate search for automatic PVARP Extension. *Memo to Brian Akers*, pp. 1–4.

Satler, L. F., Rackley, C. E., Pearle, D. L., Fletcher, R. D., and Del Negro, A. A. (1985). Inhibition of a physiologic pacing system due to its anti–pacemaker–mediated tachycardia mode. *PACE*, 8, pp. 806–810.

van Gelder, L. M., Gamal, M. I. H., Baker, R., and Sanders, R. S., (1984). Tachycardia–termination Algorithm: A valuable feature for interruption of pacemaker–mediated tachycardia. *PACE*, 7, pp. 283–287.

*Primary Examiner*—William E. Kamm
*Assistant Examiner*—Carl H. Layno
*Attorney, Agent, or Firm*—Foley & Lardner

[57] ABSTRACT

A dual chamber pulse generator senses atrial and ventricular activity of a heart and provides pacing pulses to at least a ventricle of the heart. The pulse generator includes a first detector associated with an atrium of the heart for detecting atrial activations of the heart and a second detector associated with a ventricle of the heart for detecting ventricular activations of the heart. An output applies pacing pulses to the ventricle in timed relation to atrial activations of the heart. A timer times an atrial refractory period responsive to each ventricular activation of the heart. The timer normally times an atrial refractory period of a first duration and is responsive to an extension input for timing an atrial refractory period of an extended duration longer than the first duration. The extension input is periodically provided to the timer to cause the atrial refractory period of the extended duration to be periodically timed.

21 Claims, 3 Drawing Sheets

DUAL CHAMBER PULSE GENERATOR WITH PERIODIC PMT CONTROL

BACKGROUND OF THE INVENTION

The present application generally relates to a dual chamber cardiac pulse generator. The present invention more particularly relates to an implantable dual chamber cardiac pulse generator which provides essentially periodic pacemaker mediated tachycardia (PMT) control.

Implantable pulse generators, commonly known as pacemakers, are well known in the art. Early pacemakers were single chamber pacemakers that only paced the ventricles in a trigger mode. They did not sense any cardiac activity and paced the ventricles at a predetermined, fixed rate.

Later single chamber pacemakers both sensed ventricular activity and paced the ventricles. The ventricular sensing allowed the pacemaker to inhibit pacing when a spontaneous ventricular activation (R wave) was sensed within an escape interval corresponding to a fixed pacing rate. Such pacing is referred to as demand pacing since the heart is paced only when necessary. This pacing modality is referred to in the art as VVI pacing.

As the pacemaker art advanced, dual chamber pacemakers were made available. The first dual chamber pacemakers sensed in both the atria and ventricles and paced only the ventricles. These dual chamber pacemakers, known as VDD pacemakers, were primarily for heart block patients who suffered from lack of conduction between the atria and ventricles. Their purpose was to simulate normal atrial-ventricular synchrony in heart block patients by coupling ventricular response to atrial activity. When an atrial activation (P wave) was sensed, it started the timing of an AV delay. At the end of the AV delay, the ventricles were paced. The most significant benefit of the foregoing was that when the atrial rate increased due to exercise or some other cause of increased metabolic demand, the ventricular rate would similarly increase so that the hemodynamic output of the heart would satisfy the metabolic demand. Such pacemakers could also function in a demand mode supported by ventricular sensing.

Atrial pacing was later added to the capabilities of dual chamber pacemakers. These pacemakers are referred to in the art as DDD pacemakers. They not only assist heart block patients by coupling the atria and ventricles, but further promote atrial function in sick-sinus syndrome patients whose atria generally do not function properly on their own.

Pacemakers operating in the DDD or VDD modes can, under certain circumstances, sustain a dangerous tachycardia condition. This condition, known as pacemaker mediated tachycardia (PMT) is an operational pacing state wherein the pacer erroneously stimulates the ventricle of a heart at a dangerously high rate for sustained periods of time.

Pacemaker mediated tachycardia is initiated when a ventricular activation occurs at a time during which the connective tissue between the atria and ventricles can transmit retrograde electrical signals from the ventricle to the atrium. The conduction of the ventricular signal to the atrium provides a spurious stimulation electrical signal in the atrium that appears to the pacer to be a normal atrial activation. The pacer senses this spurious retrograde atrial signal and then paces the ventricle at a predetermined AV delay time period following the sensed atrial signal. The paced ventricular signal is subsequently conducted retrograde to the atrium where it is again erroneously detected by the pacemaker as a natural atrial activation. The pacemaker therefore continues to pace the ventricle at a relatively high rate defined by the sum of the programmed AV delay time period and the retrograde conduction time between the ventricles and atria. This high rate is sustained indefinitely by the pacemaker, because retrograde conduction ensures that the pacemaker detects what appear to be high rate atrial events and tracks the spurious atrial events by generating a corresponding high rate ventricular paced stimulus. This pacemaker mediated tachycardia condition over-stimulates the heart at potential danger to the patient.

In order to preclude retrograde conducted ventricular signals from being treated by the dual chamber pacemaker as atrial activations, the post-ventricular atrial refractory period (PVARP) is employed. This timed refractory period begins upon the sensing of a natural R wave or upon a paced R wave. During these refractory periods, the atrial channel is prohibited from sensing in order to preclude sensing far field ventricular activity and creating a false atrial detection. Hence, during this time, the atrial channel cannot initiate the timing of an AV delay for the delivery of a ventricular pace. The PVARP is usually marginally maintained to be short because if set for a long duration it can limit the maximum tracking rate of the pacemaker to be too slow.

Under some conditions, PVARP alone is not adequate to preclude a PMT. A premature ventricular activation, known as a PVC, is the most common cause of PMT. A PVC is a ventricular activation that occurs out of sequence (premature) within a normal intrinsic rhythm without an intervening atrial activation. It occurs earlier than the normal sinus beat and can occur at such a time when the connective tissue between the atria and ventricles can transmit retrograde electrical signals from the ventricles to the atria. When this occurs, a PMT can be initiated even though PVARP may otherwise be adequate.

In view of the foregoing, measures have been taken in the art either to prevent a PMT condition from occurring or to terminate a PMT condition should one occur. One such measure provides for a PVARP extension whenever a PVC occurs. This precludes the need of setting PVARP so long as to adversely limit the upper tracking limit of the pacemaker while affording PMT protection from a PVC initiation. However, this requires heart activity analysis to identify a PVC which adds to the complexity of pacemakers employing this technique. In addition, if a PVC is missed, it does not alone protect against PMT.

A termination measure is the provision of PVARP extension whenever a predetermined number of consecutive ventricular paces have occurred at the pacemaker upper rate. While this does terminate a PMT, it also requires additional complexity for analyzing ventricular pacing trends and exposes the patient to this high rate.

The present invention provides a simple and elegant solution to the PMT problem. As will be seen hereinafter, the present invention prohibits an extended PMT to occur without requiring the complexities of heart activity analysis and ventricular pacing trends as have been utilized in the prior art.

SUMMARY OF THE INVENTION

The invention therefore provides a dual chamber pulse generator for sensing atrial and ventricular activity of a heart and providing pacing pulses to at least a ventricle of the heart. The pulse generator includes a first detector associated with an atrium of the heart for detecting atrial activations of the heart, a second detector associated with a ventricle of the heart for detecting ventricular activations of the heart and an output for applying pacing pulses to the ventricle in timed relation to atrial activations of the heart. The pulse generator further includes a timer to time an atrial refractory period responsive to each ventricular activation of the heart. The timer times atrial refractory periods of a first duration, and atrial refractory periods of a second duration longer than the first duration. A PVARP extension input causes the timer to periodically time an atrial refractory period of the second duration.

The invention further provides a dual chamber pulse generator for sensing atrial and ventricular activity of a heart and providing pacing pulses to at least a ventricle of the heart wherein the pulse generator includes a first detector associated with an atrium of the heart for detecting atrial activations of the heart, a second detector associated with a ventricle of the heart for detecting ventricular activations of the heart and an output for applying pacing pulses to the ventricle in timed relation to atrial activations of the heart. The pulse generator further includes a timer to time an atrial refractory period responsive to each ventricular activation of the heart. The timer normally times an atrial refractory period of a first duration and is responsive to an extension input for timing an atrial refractory period of an extended duration longer than the first duration. Extension input means periodically provides the timer with the extension input.

The present invention still further provides a dual chamber pulse generator including a first detector associated with an atrium of the heart for detecting atrial activations of the heart, a second detector associated with a ventricle of the heart for detecting ventricular activations of the heart, and an output for applying pacing pulses to the ventricle in timed relation to atrial activations of the heart. The pulse generator further includes a timer to time an atrial refractory period of a first duration responsive to a first signal and an atrial refractory period of an extended duration longer than the first duration responsive to a combination of the first signal and a second signal. The pulse generator further includes means for providing the timer with the first signal responsive to each ventricular activation at a ventricular rate and means for providing the timer with the second signal at a rate slower than the ventricular rate.

BRIEF DESCRIPTION OF THE DRAWINGS

The features of the present invention that are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENT

Figure 1:
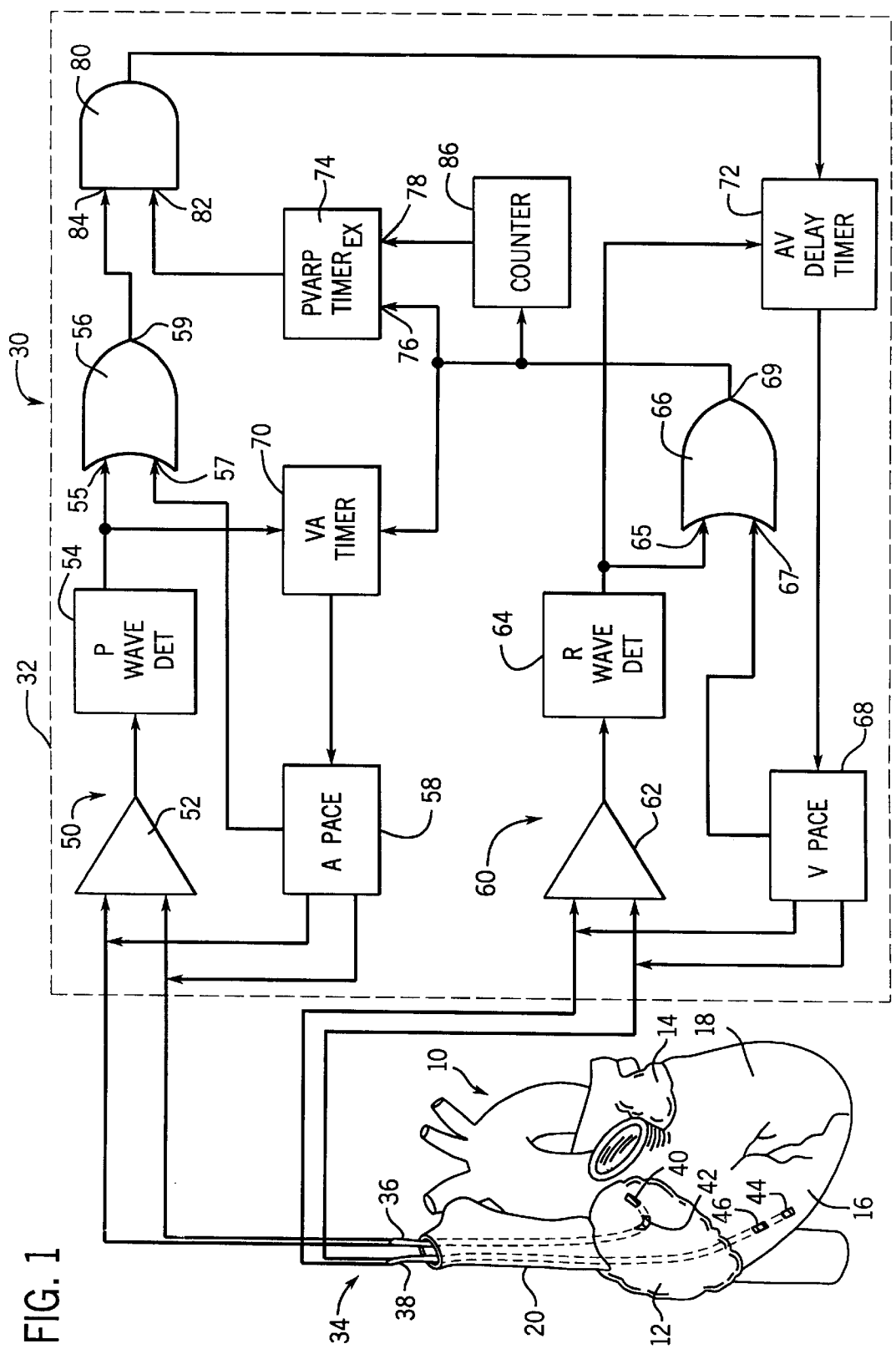
FIG. 1 is a schematic block diagram of a fully implantable dual chamber pulse generator embodying the present invention shown in association with a human heart in need of pacing management.

Referring now to FIG. 1, it illustrates a fully implantable dual chamber pulse generator 30 embodying the present invention shown in association with a human heart 10 in need of pacing management. The portions of the heart 10 illustrated in FIG. 1 and which are relevant to the understanding of the present invention are the right atrium 12, the left atrium 14, the right ventricle 16, the left ventricle 18, and the superior vena cava 20.

The dual chamber pulse generator 30 generally includes an enclosure 32 and a lead system 34 including a first endocardial lead 36 and a second endocardial lead 38. The first endocardial lead 36 is associated with the right atrium 12 of the heart 10 and includes a bipolar electrode pair including a distal or tip electrode 40 and a proximal electrode 42. The electrodes 40 and 42 are arranged to be in contact with an inner wall of the right atrium 12 to permit sensing of atrial activity. The electrodes 40 and 42 are also preferably employed for applying pacing stimuli to the atria as well.

The second endocardial lead 38 is associated with the right ventricle of the heart and includes a further bipolar electrode pair including a distal or tip electrode 44 and a proximal electrode 46. The electrodes 44 and 46 are arranged to make electrical contact with an inner wall of the right ventricle 16 to permit both the sensing of ventricular activity within the right ventricle and the application of pacing pulses to the right ventricle.

Within the enclosure 32 the pulse generator 30 includes an atrial channel 50 and a ventricular channel 60. The atrial channel 50 includes a sense amplifier 52 of a type well known in the art and a P wave detector 54. The P wave detector 54 preferably includes a threshold detector as is well known in the art. The ventricular channel 60 includes a sense amplifier 62 of the type well known in the art and an R wave detector 64. Like the P wave detector 54, the R wave detector 64 preferably includes a threshold detector as is also well known in the art.

As used herein, the term "atrial activation" is used to denote a P wave of the heart whether occurring naturally or spontaneously or as a result of an atrial pacing stimulus. Similarly, the term "ventricular activation" is used to denote an R wave of the heart whether occurring normally or spontaneously or as a result of the application of a ventricular pacing stimulus.

The electrodes 40 and 42 of the endocardial lead 36 are coupled to the sense amplifier 52. The sense amplifier 52 senses atrial activity of the heart 10. The output of the sense amplifier 52 is coupled to the P wave detector 54 that, from the atrial activity sensed by the sense amplifier 52, detects atrial activations of the atria. The output of the P wave detector 54 is coupled to an input 55 of an ORgate 56.

The pulse generator 30 further includes an atrial pace output circuit 58. The atrial pace output circuit 58 has a pair of outputs which are coupled to the electrodes 40 and 42 of the endocardial lead 36 for applying atrial pacing stimuli to the atria. The atrial pace output circuit 58 also makes an input to an input 57 of ORgate 56 whenever an atrial pacing stimulus is applied to the atria. As a result, the output 59 of the ORgate 56 provides an output signal whenever an atrial activation occurs spontaneously or by virtue of a pacing stimuli being applied to the atria.

The electrodes 44 and 46 of the endocardial lead 38 are coupled to the inputs of the ventricular sense amplifier 62. The sense amplifier 62 hence senses ventricular activity of the heart 10. The output of the sense amplifier 62 is coupled to the R wave detector 64. The R wave detector 64 detects ventricular activations from the ventricular activity sensed by the sense amplifier 62. Whenever the R wave detector 64 detects a ventricular activation, it provides a signal to an input 65 of an ORgate 66.

The pulse generator 30 further includes a ventricular pace output circuit 68. The ventricular pace output circuit 68 is coupled to the electrodes 44 and 46 of the endocardial lead 38 for applying ventricular pacing pulses or stimuli to the ventricles. The ventricular pace output circuit 68 makes input to the ORgate 66 at an input 67 whenever a ventricular pacing stimulus is applied to the electrodes 44 and 46. As a result, the ORgate 66 provides at an output 69 an output signal whenever a normal or spontaneous ventricular activation occurs or when a ventricular activation occurs by virtue of a pacing stimulus being applied to the ventricles by the ventricular pace output circuit 68.

The pulse generator 30 further includes a VA timer 70. The VA timer 70 times an escape interval for the atrial pace output circuit 58. When a ventricular activation occurs, the output of the ORgate 69 causes the VA timer to begin timing a VA interval. The VA interval may be, for example, 700 to 800 milliseconds. At the conclusion of the VA time period, the VA timer provides a signal to the atrial pace output circuit 58 to cause the atrial pace output circuit 58 to deliver a pacing stimulus to the electrodes 40 and 42 and thus to the atria. The output of the P wave detector 54 in addition to being coupled to input 55 of ORgate 56 is further coupled to an input of the VA timer 70. If, during the timing of the VA time period, the P wave detector 54 detects an intrinsic or spontaneous atrial activation, it will provide a reset input to the VA timer to reset the VA timer 70 to cause the atrial phase output circuit 58 to be inhibited and to thereby preclude the atrial pacing stimulus from being applied to the atria. This will be recognized by those skilled in the art as demand pacing.

The pulse generator 30 still further includes an AV delay timer 72 that times an AV delay time period which commences from an atrial activation and extends for a predetermined AV delay time period of, for example, 100 to 150 milliseconds. At the end of the AV delay time period, the AV delay timer 72 provides an input to the ventricular pace output circuit 68 to cause the ventricular pace output circuit 68 to deliver a pacing stimulus to electrodes 44 and 46 of the endocardial lead 38 and thus to the ventricles. If during the timing of the AV delay time period the R wave detector 64 detects an intrinsic or spontaneous ventricular activation, it will provide an input to the AV delay timer 72 to reset the AV delay timer 72. This inhibits the ventricular pace output circuit 68 and precludes a ventricular pacing stimulus from being applied to the ventricles by the ventricular pace output circuit 68. This will also be recognized by those skilled in the art as demand pacing.

In accordance with the present invention, the pulse generator 32 includes a post-ventricular atrial refractory period (PVARP) timer 74. The PVARP timer 74 has a first input 76 which is coupled to the output 69 of the ORgate 66. Whenever a ventricular activation occurs, the ORgate 66 at output 69 causes the PVARP timer 74 to begin timing the PVARP. During the time in which the PVARP timer 74 is timing the PVARP, it will provide a low logic signal to an input 82 of ANDgate 80.

The output 59 of ORgate 56 is coupled to the other input 84 of ANDgate 80. The ANDgate 80 produces a signal to cause the AV delay timer 72 to begin timing an AV delay time period when a ventricular activation occurs at a time when the PVARP timer 74 is not timing the PVARP. Hence, during the PVARP, the ANDgate 80 is precluded from providing such a signal to the AV delay timer 72 responsive to an atrial activation. However, it will provide such a signal to cause the AV delay timer 72 to begin timing an AV delay time period if an atrial activation occurs after the PVARP timer has timed the PVARP.

The PVARP timer has a second input 78 which is coupled to the output of a counter 86. The counter 86 has an input which is coupled to the output 69 of ORgate 66. The counter 86 is preferably of the type which provides an output to the second or extension input 78 of the PVARP timer 74 every n ventricular activations. For example, the counter 86 may provide an output to the second input 78 of the PVARP timer 74 every tenth ventricular activation. Because the counter is coupled to the output 69 of ORgate 66, it will provide such a signal to the PVARP timer 74 after the predetermined number of consecutive ventricular activations, whether the ventricular activations are intrinsic or spontaneous activations or the result of a ventricular pacing stimulus.

The PVARP timer 74, in accordance with the present invention, times atrial refractory periods of a first duration responsive to receiving an input signal at its first input 76 from ORgate 66 and atrial refractory periods of a second duration, longer than the first duration, responsive to receiving inputs at its first input 76 from the ORgate 66 together with an input at its second or extension input 78 from the counter 86. For example, the first PVARP may be on the order of 100 milliseconds while the extended PVARP may be on the order of 150 milliseconds. As a result of the foregoing, the PVARP timer will periodically time an atrial refractory period of the extended or second duration. The periodicity of the extended PVARP timing is provided by the counter 86. As a result, it receives at its first input 76 a first signal from ORgate 66 at the ventricular rate and a second signal at its input 78 at a rate which is less than the ventricular rate.

By virtue of the foregoing, the PVARP of the pulse generator 30 is periodically extended. Such periodic extension does not require the previously mentioned analysis required by the prior art thus rendering the PVARP extension of the present invention substantially less complicated to implement. At the same time, pacemaker mediated tachycardia is effectively managed.

Figure 2:
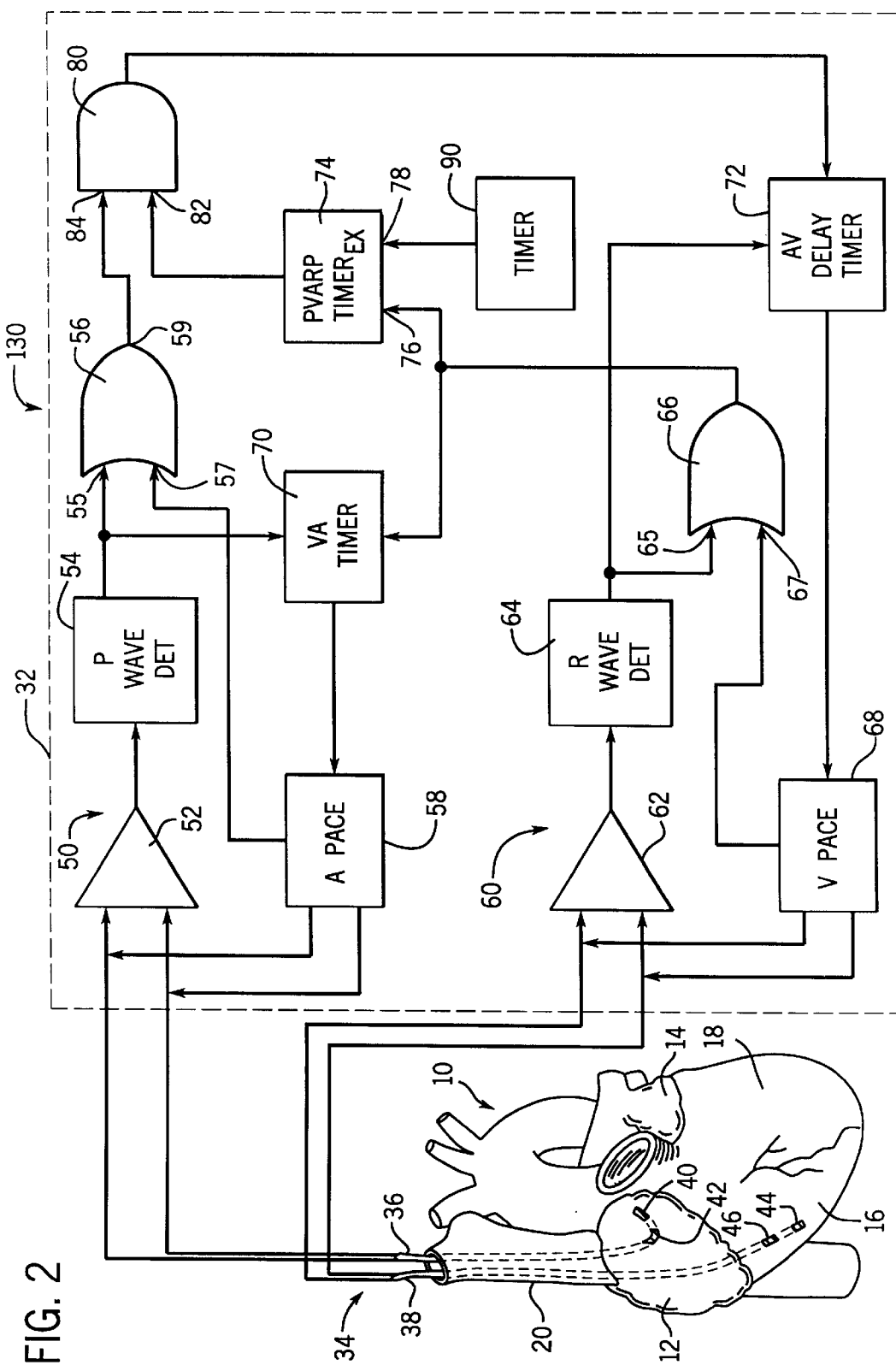
FIG. 2 is a schematic block diagram of another fully implantable dual chamber pulse generator in accordance with a second embodiment of the present invention associated with a human heart in need of pacing management.

Referring now to FIG. 2, it illustrates another dual chamber pulse generator 130 embodying the present invention. The pulse generator 130 is substantially similar to the pulse generator 30 of FIG. 1 and to the extent that it includes identical elements, identical reference numerals have been maintained.

Instead of incorporating the counter 86 of the embodiment of FIG. 1, the pulse generator 130 of FIG. 2 includes a timer 90 to provide the periodic extension of the PVARP. As can be seen in FIG. 2, the pulse generator 130 includes a timer 190 which provides an input to the second or extension input 78 of the PVARP timer 74. The timer 90 times predetermined consecutive time intervals. As a result, every n seconds, for example every 10 seconds, the timer 90 will provide an input to input 78 of PVARP timer 74. This will cause the PVARP timer 74 to time the extended PVARP upon the next input from ORgate 66 to its first input 76. As a result of the foregoing, the PVARP of the pulse generator 130 is periodically extended after every so many seconds.

Figure 3:
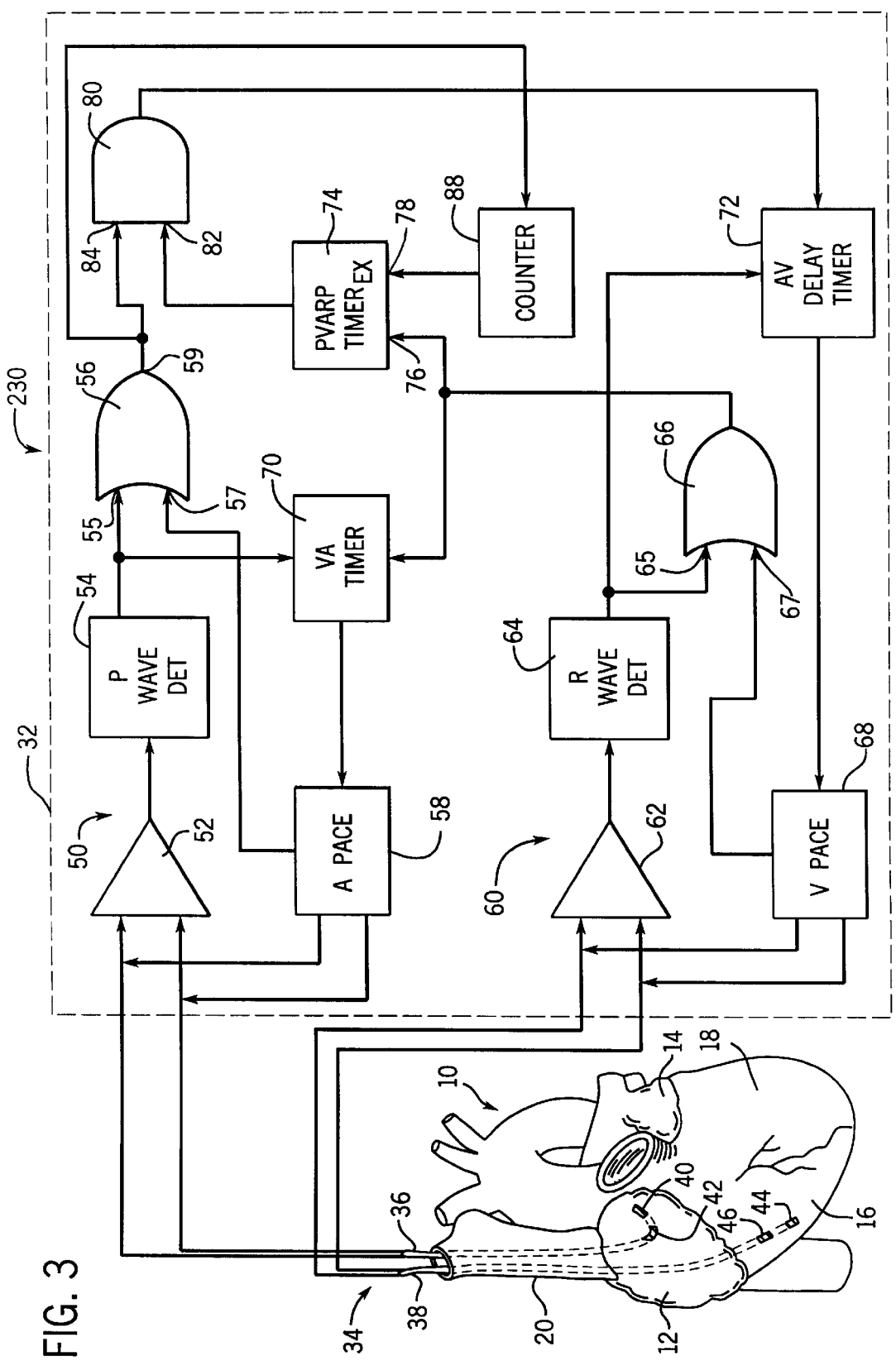
FIG. 3 is a schematic block diagram of a further dual chamber pulse generator embodying the present invention in accordance with a further alternative embodiment in association with a human heart in need of pacing management.

Referring lastly to FIG. 3, it illustrates a still further pulse generator 230 embodying a further embodiment of the present invention. Again, the pulse generator 230 is substantially similar to the pulse generator 30 of FIG. 1, and to the extent that it includes identical elements, identical reference characters have been maintained. Here, the pulse generator 230 includes a counter 88 similar to counter 86 of the embodiment of FIG. 1 except that the counter 88 receives an input from the output 59 of ORgate 56. Whenever an atrial activation occurs, the counter 88 receives a new input. As a result, the counter 88 provides a signal to the second or extension input 78 of PVARP timer 74 every n atrial activations. The ventricular activation occurring immediately after every $n^{th}$ atrial activation will cause the PVARP timer 74 to time the extended PVARP. Again, the embodiment of FIG. 3 provides periodic extension of the PVARP.

While particular embodiments of the present invention have been shown and described, modifications may be made, and it is therefore intended in the appended claims to cover all such changes and modifications which fall within the true spirit and scope of the invention.

What is claimed is:

1. A dual chamber pulse generator for sensing atrial and ventricular activity of a heart and providing pacing pulses to at least a ventricle of the heart, the pulse generator comprising;

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period responsive to each ventricular activation of the heart, the timer timing atrial refractory periods of a first duration and atrial refractory periods of a second duration longer than the first duration; and means for causing the timer to periodically time an atrial refractory period of the second duration.

2. A pulse generator as defined in claim 1 wherein the means for causing includes a counter for causing the timer to time an atrial refractory period of the second duration responsive to every $n^{th}$ ventricular activation.

3. A pulse generator as defined in claim 1 wherein the means for causing includes a second timer for causing the timer to time an atrial refractory period of the second duration upon a first ventricular activation occurring after every one of successive predetermined time periods.

4. A pulse generator as defined in claim 1 wherein the means for causing includes a counter for causing the timer to time an atrial refractory period of the second duration upon a first ventricular activation occurring after every $n^{th}$ atrial activation.

5. A pulse generator as defined in claim 1 wherein the means for causing includes means for causing the timer to periodically time an atrial refractory period of the second duration at fixed intervals of time.

6. A pulse generator as defined in claim 1 wherein the means for causing includes means for causing the timer to periodically time an atrial refractory period of the second duration at times based upon the number of detected atrial or ventricular activations.

7. A dual chamber pulse generator for sensing atrial and ventricular activity of a heart and providing pacing pulses to at least a ventricle of the heart, the pulse generator comprising:

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period responsive to each ventricular activation of the heart, the timer normally timing an atrial refractory period of a first duration and being responsive to an extension input for timing an atrial refractory period of an extended duration longer than the first duration; and extension input means for periodically providing the timer with the extension input at a rate lower than a ventricular rate.

8. A pulse generator as defined in claim 7 wherein the extension input means includes means for periodically providing the timer with the extension input at fixed intervals of time.

9. A pulse generator as defined in claim 7 wherein the extension input means includes means for periodically providing the timer with the extension input at times based upon the number of detected atrial or ventricular activations.

10. A dual chamber pulse generator for sensing atrial and ventricular activity of a heart and providing pacing pulses to at least a ventricle of the heart, the pulse generator comprising:

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period responsive to each ventricular activation of the heart, the timer normally timing an atrial refractory period of a first duration and being responsive to an extension input for timing an atrial refractory period of an extended duration longer than the first duration; and extension input means for periodically providing the timer with the extension input including a counter for counting the ventricular activations and providing the extension input every $n^{th}$ ventricular activation.

11. A dual chamber pulse generator for sensing atrial and ventricular activity of a heart and providing pacing pulses to at least a ventricle of the heart, the pulse generator comprising:

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period responsive to each ventricular activation of the heart, the timer normally timing an atrial refractory period of a first duration and being responsive to an extension input for timing an atrial refractory period of an extended duration longer than the first duration; and extension input means for periodically providing the timer with the extension input including a second timer for providing the extension input at the end of spaced apart time intervals after every time period.

12. A dual chamber pulse generator for sensing atrial and ventricular activity of a heart and providing pacing pulses to at least a ventricle of the heart, the pulse generator comprising:

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period responsive to each ventricular activation of the heart, the timer normally timing an atrial refractory period of a first duration and being responsive to an extension input for timing an atrial refractory period of an extended duration longer than the first duration; and extension input means for periodically providing the timer with the extension input including a counter for counting the atrial activations and providing the extension input every $n^{th}$ atrial activation.

13. A dual chamber pulse generator for sensing atrial and ventricular activity of a heart and providing pacing pulses to at least a ventricle of the heart, the pulse generator comprising:

a first detector associated with an atrium of the heart for detecting atrial activations of the heart;

a second detector associated with a ventricle of the heart for detecting ventricular activations of the heart;

an output for applying pacing pulses to the ventricle in timed relation to atrial activations of the heart;

a timer to time an atrial refractory period of a first duration responsive to a first signal and an atrial refractory period of an extended duration longer than the first duration responsive to a combination of the first signal and a second signal;

means for providing the timer with the first signal responsive to each ventricular activation at a ventricular rate; and means for providing the timer with the second signal periodically at a rate lower than the ventricular rate.

14. A pulse generator as defined in claim 13 wherein the means for providing the timer with the second signal includes means for providing the timer with the second signal periodically at fixed intervals of time.

15. A pulse generator as defined in claim 13 wherein the means for providing the timer with the second signal includes means for providing the timer with the second signal periodically at times based upon the number of detected atrial or ventricular activations.

16. A method for sensing atrial and ventricular activity of a heart and providing pacing pulses to at least a ventricle of the heart, comprising the steps of:

detecting atrial activations of the heart;

detecting ventricular activations of the heart;

applying pacing pulses to the ventricle in timed relation to atrial activations of the heart;

timing an atrial refractory period responsive to each ventricular activation of the heart including the steps of timing atrial refractory periods of a first duration and timing atrial refractory periods of a second duration longer than the first duration; and timing the atrial refractory period of the second duration periodically.

17. The method of claim 16 wherein the step of timing the atrial refractory period of the second duration periodically includes the steps of counting ventricular activations and timing an atrial refractory period of the second duration responsive to every $n^{th}$ ventricular activation.

18. The method of claim 16 wherein the step of timing the atrial refractory period of the second duration periodically includes the steps of timing a predetermined time period and timing an atrial refractory period of the second duration upon a first ventricular activation occurring after every one of successive predetermined time periods.

19. The method of claim 16 wherein the step of timing the atrial refractory period of the second duration periodically includes the steps of counting atrial activations and timing an atrial refractory period of the second duration upon a first ventricular activation occurring after every $n^{th}$ atrial activation.

20. The method of claim 16 wherein the step of timing the atrial refractory period of the second duration includes the step of timing the atrial refractory period of the second duration periodically at fixed intervals of time.

21. The method of claim 16 wherein the step of timing the atrial refractory period of the second duration includes the step of timing the atrial refractory period of the second duration periodically at times based upon the number of detected atrial or ventricular activations.

* * * * *